United States Patent [19]

Frangione

[11] Patent Number: 5,782,992
[45] Date of Patent: Jul. 21, 1998

[54] CONTACT LENS DISINFECTING SOLUTION CONTAINING SODIUM CHLORITE AND POLYVINYL PYRROLIDONE

[75] Inventor: Anthony P. Frangione, Rancho Santa Margarita, Calif.

[73] Assignee: Allergan, Waco, Tex.

[21] Appl. No.: 219,004

[22] Filed: Mar. 29, 1994

Related U.S. Application Data

[63] Continuation of Ser. No. 991,775, Dec. 17, 1992, abandoned.

[51] Int. Cl.$^6$ .................... A61L 2/18; A61K 31/79; A61K 33/20; A61N 59/00
[52] U.S. Cl. .................... 134/42; 510/112; 510/115; 514/839; 514/84; 134/26
[58] Field of Search .................... 252/106, 102, 252/542; 514/840, 839; 510/115, 112; 134/26, 42

[56] References Cited

U.S. PATENT DOCUMENTS

| | | | |
|---|---|---|---|
| 3,920,810 | 11/1975 | Rankin | 424/78.04 |
| 4,407,791 | 10/1983 | Stark | 424/80 |
| 4,499,077 | 2/1985 | Stockel et al. | 424/149 |
| 4,525,346 | 6/1985 | Stark | 424/80 |
| 4,529,535 | 7/1985 | Sherman | 252/106 |
| 4,537,746 | 8/1985 | Ogunbiyi et al. | 422/28 |
| 4,642,234 | 2/1987 | Davies et al. | 424/78 |
| 4,654,208 | 3/1987 | Stockel et al. | 424/78 |
| 4,731,192 | 3/1988 | Kenjo et al. | 252/95 |
| 4,731,193 | 3/1988 | Mason et al. | 252/95 |
| 4,758,595 | 7/1988 | Ogunbiyi et al. | 514/638 |
| 4,767,559 | 8/1988 | Kruse et al. | 252/106 |
| 4,775,424 | 10/1988 | Wisotzki et al. | 134/42 |
| 4,829,129 | 5/1989 | Kelley | 525/362.9 |
| 4,836,986 | 6/1989 | Ogunbiyi et al. | 422/28 |
| 4,861,514 | 8/1989 | Hutchings | 134/42 |
| 4,889,654 | 12/1989 | Mason et al. | 252/100 |
| 4,977,179 | 12/1990 | Nakamura et al. | 422/71 |
| 4,986,990 | 1/1991 | Davidson et al. | 422/665 |
| 4,997,626 | 3/1991 | Dzabo et al. | 422/37 |
| 5,008,106 | 4/1991 | Merianos et al. | 424/80 |
| 5,019,380 | 5/1991 | Heiler | 424/81 |
| 5,078,908 | 1/1992 | Ripley et al. | 252/187.1 |
| 5,091,107 | 2/1992 | Hutchings | 134/37 |
| 5,424,078 | 6/1995 | Dziabo et al. | 424/661 |

FOREIGN PATENT DOCUMENTS

| 0454441 | 10/1991 | European Pat. Off. . |
|---|---|---|
| 0458578 | 11/1991 | European Pat. Off. . |

OTHER PUBLICATIONS

"Kollidon grades"; Technical Information; NEF 129e; Dec. 1990 (ATM).

PCT International Search Report, International Application No. PCT/US93/11734 (corresponding to parent U.S. application Serial No. 07/991,775) Mar. 12, 1993.

Dalcanale, Enrico; Montanari, Fernando; "Selective Oxidation of Aldehydes to Carboxylic Acids with Sodium Chlorite–Hydrogen Peroxide"; J. Org. Chem., 1986, 51, 567–569 no month available.

"PVP–Iodine grades"; Technical Information; MEF 141 e (897) Jan. 1991; Register 4; BASF.

"Kollidon® grades"; Technical Information; MEF 129 e (889) Dec. 1990 (AJM); Register 2; BASF.

*Primary Examiner*—Douglas J. McGinty
*Assistant Examiner*—Necholus Ogden
*Attorney, Agent, or Firm*—Carlos A. Fisher

[57] ABSTRACT

An ophthalmically acceptable solution and a method useful for disinfecting and/or cleaning a contact lens. The solution comprises an oxidizing agent and a polyvinyl pyrrolidone having a molecular weight ranging from 10,000 to 100,000 daltons and reactive towards a chlorite oxidizing agent. The end groups of the polyvinyl pyrrolidone are preferably aldehydes. The oxidizing agent of this invention preferably is selected from the group comprising chlorine oxides. The solution preferably has a pH ranging from about 6 to about 8.5. The method of the invention comprises the steps of forming this solution and then contacting a contact lens with the solution.

8 Claims, No Drawings

CONTACT LENS DISINFECTING SOLUTION CONTAINING SODIUM CHLORITE AND POLYVINYL PYRROLIDONE

This application is a continuation of application Ser. No. 07/991,775, filed Dec. 17, 1992, now abandoned.

BACKGROUND OF THE INVENTION

1. Field of the Invention

This invention relates generally to compositions for and a method of disinfecting contact lenses. More particularly, the present invention is directed to an ophthalmically acceptable contact lens solution comprising an oxidizing agent and a polyvinyl pyrrolidone having a molecular weight ranging from about 10,000 to about 100,000 daltons and having a reactive end group.

2. Description of Related Art

During the normal course of handling and wearing contact lenses, especially lenses made from hydrophilic materials, pathogenic agents or microorganisms typically accumulate and grow on the lenses. The presence of these pathogens on contact lenses oftentimes results in wearer discomfort and may even result in a contact lens wearer's eyes becoming infected. Therefore, in order to protect the wearer's eyes from infection and to enhance the wearer's comfort, contact lenses should be continuously disinfected to kill any harmful microorganisms that may be present on the lenses. Two such microorganism which are incorporated into the panel of microorganisms required by the 1985 U.S. Food and Drug Administration guidelines for contact lens solutions for disinfection efficacy includes *Candida albicans* (*C. albicans*) (ATCC 10231) and *Aspergillus fumigatus* (*A. fumigatus*) (ATCC 10894), a fungus.

It is well known that the oxidizing agent chlorine dioxide possesses a powerful killing effect on bacteria, fungi, viruses and spores. Aqueous solutions of chlorine dioxide, however, are relatively unstable and rapidly lose chlorine dioxide because chlorine dioxide is gaseous at atmospheric pressure and ambient temperature and, thus, the antimicrobial efficacy of such solutions are relatively short-lived.

Stabilized chlorine dioxide, on the other hand, has germicidal properties and fewer of the disadvantages of chlorine dioxide gas. For example, solutions of stabilized chlorine dioxide have less antimicrobial efficacy but possess a longer shelf life than aqueous solutions of chlorine dioxide.

A stabilized chlorine dioxide solution can be obtained by passing gaseous chlorine dioxide into an aqueous solution containing 12% $Na_2CO_3 \cdot 3H_2O_2$, at pH 6 to 8. It has also been shown in U.S. Pat. No. 4,829,129 to Kelley that a microbiocidal composition may be formed by reacting gaseous chlorine dioxide with a wide range of equivalent polymeric N-vinyl-α-pyrrolidones ("PVP").

PVP is used in ophthalmic preparations in order to increase viscosity, for example, in eye drops. In some eye drops PVP is used to prolong the therapeutic action of substances such as pilocarpine and to promote the bioavailability of drugs. PVP is also used in fluids for contact lenses. Various grades of PVP are commercially available from BASF Aktiegensellchaft of Ludwigshafen, Germany under the name of Kollidon®. For example, the following grades of Kollidon® are water soluble forms of PVP: K-12 PF (molecular weight≈2,900); K-17 PF (molecular weight≈9,000); K-25 (molecular weight≈29,000); K-30 (molecular weight≈45,000); and K-90 (molecular weight≈1,100,000).

It has only been discovered within about the last ten years that stabilized chlorine dioxide may be used as an antimicrobial agent for soft contact lenses. U.S. Pat. No. 4,499,077 to Stockel discloses an antimicrobial composition for soft contact lenses including an oxidizing agent such as an oxyhalogen compound, e.g., stabilized chlorine dioxide or hydrogen peroxide, and a polymeric germicide, e.g., a quaternary ammonium polymer or an amino and/or imino polymer or salts thereof.

U.S. Pat. No. 4,654,208 to Stockel discloses an antimicrobial composition for contact lenses including an aqueous solution of a germicidal polymeric nitrogen compound and an oxidizing agent, e.g., chlorine dioxide, chlorite, stabilized chlorine dioxide or hydrogen peroxide, to potentiate the activity of the germicidal polymeric nitrogen compound at low concentrations. The Stockel patents characterize the polymeric germicides and the germicidal polymeric nitrogen compounds as positively charged, nitrogen-containing cationic polymers and polymeric amino and/or imino compounds.

U.S. Pat. No. 4,731,192 to Kenjo discloses a two-part composition cleaning system for contact lenses wherein free oxygen is released when a composition containing a chlorite salt, in aqueous solution, and a solid composition containing solid acid or organic salt, an oxygen-consuming agent, and a polyvinyl pyrrolidone are combined. Reducing sugars may be included with the solid composition part. Kenjo compositions however suffer from the problem of short shelf life.

U.S. Pat. No. 4,731,193 to Mason discloses another two-part aqueous disinfection composition which comprises a foaming agent such as a nonionic surfactant including polyvinyl alcohol, polyvinyl pyrrolidone and nonylphenoxy polyethanol. Chlorine dioxide is then added to the solution or it is generated in situ by reacting an oxidizing agent, a cationic exchange resin in the acidic form, or an acid with a metal chlorite such as lithium chlorite, sodium chlorite or potassium chlorite.

Quite clearly, with respect to Mason and Kenjo, the need to admix two parts to achieve a final composition is undesirable. A level of sophistication is needed by the ultimate user, lest incorrectly mixed dosage amounts of the two portions provide too little or too much chlorine dioxide. Alternatively, special packaging for mixing aliquot amounts of the two premixes is needed, which special packaging raises the cost of the final product to the ultimate user.

Another recently discovered problem with contact lens disinfecting working solutions containing PVP and some oxidizing agents is that in a short period of time during the typical regimen, some of such solutions do not show significant effectiveness as against *C. albicans* and *A. fumigatus*.

Also, sodium chlorite is known to react with aldehydes in the presence of peroxide.

There continues to be a need for an easy to use and relatively inexpensive ophthalmically safe solution for use with contact lenses which offers enhanced antimicrobial activity, especially with respect to *C. albicans* and *A. fumigatus*, and an improved stability and shelf life.

SUMMARY OF THE INVENTION

After intensive investigations made for the purpose of overcoming the defects of the conventional disinfecting solutions currently used, the inventors have unexpectedly discovered that an ophthalmic solution which exhibits superior disinfection efficacy, an improved stability and thus increased shelf life may be formed by adding a specific type of water soluble PVP that reacts with an oxidizing agent in a solution having such an oxidizing agent, preferably a chlorite ion based oxidizing agent.

According to a broad aspect of the present invention, an ophthalmically acceptable solution for use with contact lenses is provided comprising an oxidizing agent and a specific type of PVP, i.e., one having a molecular weight ranging from about 10,000 to about 100,000 daltons and having reactivity with an oxidizing agent. The PVP is preferably selected from PVP's having reactive end groups wherein such reactive end groups are preferably selected from the group consisting of aldehyde, acids, primary and secondary hydroxyls, amine, vinyl, (ethylene) acetylene, ethynyl and mixtures thereof.

The present invention is also directed to a method of disinfecting and/or cleaning a contact lens. In a broad aspect, the method of the present invention comprises the steps of forming an ophthalmically acceptable solution comprising an oxidizing agent and a PVP having a molecular weight ranging from about 10,000 to about 100,000 daltons being reactive with an oxidizing agent. Subsequently, a contact lens is contacted with the solution for a period of time sufficient to disinfect the lens.

DETAILED DESCRIPTION OF THE INVENTION

The present invention is directed to a new ophthalmically safe solution which exhibits superior microbiocidal activity and also preferably possesses a shelf life (i.e., activity against selected microbes), at room temperature, of at least about 18 months. More preferably, the solution of this invention is extremely effective in killing C. albicans (ATCC 10231) and possesses an average shelf life of about two years. The present invention is also directed to a rapid one-step procedure for disinfecting and/or rinsing a contact lens or lenses.

The present invention can be used with all contact lenses such as conventional hard, soft, rigid, gas permeable and silicone lenses, but it is preferably employed with soft contact lenses such as those commonly referred to as hydrogel lenses prepared from monomers such as hydroxyethylmethacrylate, hydroxyethylmethyl methacrylate, vinylpyrrolidone, glyceromethacrylate, methacrylate or acid esters and the like.

In one embodiment, the present invention involves an ophthalmically acceptable solution for use with contact lenses comprising an oxidizing agent and a specific type of PVP which has a molecular weight ranging from about 10,000 to about 100,000 and is reactive with an oxidizing agent in solution. Preferably, the oxidizing agent of the present invention is selected from the group consisting of chlorine oxides wherein the chlorine oxides include a source of chlorite ions ($ClO_2^-$). Examples of sources of $ClO_2^-$ include, but are not limited to, alkali metal salts, e.g., lithium salts and potassium salts, and alkaline earth salts, e.g., calcium salts. Stabilized chlorine dioxide, may also be used as a source of $ClO_2$. Stabilized chlorine dioxide is commercially available as Purite™ which is manufactured by Biocide, of Norman, Okla. Preferably, the solution of the present invention comprises sodium chlorite as a source of $ClO_2^-$.

Provided below is a chart converting Purite™ concentrations to chlorite concentrations and vice versa.

1 ppm Purite™=1 ppm stabilized chlorine dioxide 1 ppm Purite™=1.25 ppm chlorite ion 1 ppm Purite™=1.6761 ppm sodium chlorite 1 ppm Purite™=2.1216 ppm technical grade* sodium chlorite Technical grade sodium chlorite contains about 80% $NaClO_2$, 13% NaCl, 5% $Na_2CO_3$ and 2% $NaClO_3$.

If sodium chlorite is used as the source of chlorite ions in the solution, generally there is present in the solution from about 0.008% (w/v) to about 0.3% (w/v) sodium chlorite. Preferably, there is present from about 0.02% (w/v) to about 0.08% (w/v), and more preferably from about 0.025% (w/v) to about 0.05% (w/v) sodium chlorite in the solution.

Alternatively, the solution of this invention may include stabilized chlorine dioxide or Purite™ as a source of chlorite ions. In this embodiment, generally there is from about 0.005% (w/v) to about 0.2% (w/v) stabilized chlorine dioxide in the solution. Preferably, there is present from about 0.01 % (w/v) to about 0.05% (w/v), and even more preferably about 0.015% (w/v) to about 0.03% (w/v) stabilized chlorine dioxide present in the solution.

A significant aspect of this invention is that the solution also comprises a specific type or grade of PVP. Applicants have found to their surprise that by using a specific grade of PVP at concentrations greater than at least about 0.25% (w/v) in the solution, the anti-microbial efficacy of the ophthalmic solution is greatly improved.

In the present invention the specific grade of PVP has a molecular weight ranging from about 10,000 to about 100,000 daltons, and more preferably from about 10,000 to about 50,000 daltons, and even more preferably from about 29,000 to about 45,000 daltons.

Further, it is important that the PVP of the present invention be generally one that is reactive with an oxidizing agent and preferably toward chlorite or stabilized chlorine dioxide. More preferably, the PVP includes a reactive end group (hereinafter "reactive end group PVP") wherein the reactive end group is preferably selected from the group consisting of aldehyde, acid, primary and secondary hydroxyls, amine, vinyl, (ethylene), acetylene, ethylyne and mixtures thereof. More preferably the reactive end group is aldehyde.

Exemplary polymers capable of forming the same type reaction product with $ClO_2^-$ besides PVP include water soluble copolymers of vinylpyrrolidone with vinyl pyridine, acrylamide, substituted acrylamides, vinyl caprolactam, vinyl phthalamide, etc. Also homopolymers such as polyvinyl caprolactam, polyvinyl-α-valerolactam, polyvinyl-a-valerolactam, and the like. These polymers are expected to exhibit the same type of behavior to a greater or lesser degree depending upon the particular polymer chosen.

It is also preferred that at least about 50% of the end groups are reactive.

More preferably, at least about 80% of the end groups of the reactive end group PVP are reactive, and even more preferably about 100% of the end groups are reactive. With respect to certain functional end groups such as alcohols, tertiary alcohol end groups are not particularly reactive, for example, t-butyl alcohol.

More specifically, it is preferred that K-25 and K-30 be used as the source of reactive end group PVP in the invention because it is believed that these grades of polyvinyl pyrrolidone include aldehyde end groups which are reactive with the oxidant of the present invention. K-25 and K-30 grades of reactive end group PVP are well known and are obtained by using acetylaldehyde to terminate the polymerization reaction.

The solution of the present invention contains about 0.25 to about 4.0% (w/v) of reactive end group PVP. More preferably the solution contains about 0.25 to about 2.0% (w/v) and preferably still from about 0.4 to about 2.0% (w/v) of reactive end group PVP, and even more preferably from about 0.5% to about 1.5% (w/v) of reactive end group PVP. If greater than 2.0% PVP is used, for example 4.0%, a strong buffering agent must be added to the solution.

The pH of the solution of the present invention preferably ranges from about 6.0 to about 8.5, and more preferably the solution should be at physiological pH, i.e., about 7.0 to about 7.4. If the pH of the solution is less than about 6, spontaneous degeneration of chlorite or stabilized $ClO_2$ may occur causing the shelf life of the solution to significantly decrease.

In order to maintain the desired pH of the solution, it may be necessary to add a buffering agent to the solution. Examples of suitable buffering agents which may be added to the solution include, but are not limited to, alkali metal salts such as potassium or sodium carbonates, acetates, borates, phosphates, tartrates, citrates and hydroxides, and relatively weak acids such as acetic and boric acids. Preferred buffering agents are boric acid/borate buffers such as boric acid, sodium borate decahydrate and mixtures thereof. The amount of buffering agent used should be sufficient to provide the desired pH of the solution. Preferably, there is a total borate concentration of 0.2% (w/v) to about 2.0% (w/v) and more preferably 0.5% to 1.0%.

In the solution of the present invention there is preferably further present an amount of chloride salt sufficient to make the solution isotonic. It is preferred that the tonicity of the disinfecting solution of this invention ranges from about 270 to about 330 mOsm. Preferably the solution includes chloride salts such as sodium chloride and potassium chloride sufficient to make the solution isotonic.

Other additives to the disinfecting solution of the present invention include, but are not limited to, conventional lens solution cleaning and soaking solution additives. Preservatives such as benzylalkonium chloride and ethylenediaminetetraacetic acid (EDTA) can be used. Wetting agents such as hydroxypropyl methylcellulose and methylcellulose can be used. This solution may also contain carboxymethylcellulose. The solution may also include surfactants such as alkyl sulphonates and alkyl glucosides. Further, the disinfecting solution of this invention may include other disinfecting agents so long as these agents do not destabilize the oxidant. Examples of additional disinfecting agents which may be used include, but are not limited to, polyquaternary amines, e.g., Croquat™ L which is commercially available from Croda, Inc. Croquat™ is a quaternary ammonium substituted polypeptide which is based on a collagen hydrosylate of relatively low molecular weight, includes lauryl trimethyl ammonium chloride groups and has a molecular weight in the range of about 500 to about 5000. Disinfecting agents such as biguanides, peroxide, and water soluble cationic polymers (WSCP) which are available from Buckman Laboratories, Inc. and are described in U.S. Pat. No. 4,250,269, which is incorporated herein by this reference, may also be used in the present invention. The additives, set forth above, are used in a wide range of concentrations as known in the art. Preferably, the pH of the solutions of this invention are as near to physiological pH as possible and always in the range of about pH 6–8.5.

The following detailed Example is a presently preferred composition for the ophthalmic solution of the instant invention. However, it is to be understood that this Example is for illustrative purposes only and is not intended to limit the scope of the ophthalmic solution of the present invention.

EXAMPLE 1

| Ingredients | % (w/v) |
|---|---|
| Sodium chloride | 0.62 |
| Boric acid | 0.473 |
| Sodium borate decahydrate | 0.090 |
| Sodium chlorite* | 0.0214 |
| PVP** | 0.50 |

*Sodium chlorite may be substituted with 0.0178% (w/v) Purite ™
**The following grades of PVP can be substituted for one another: K-25 or K-30 or mixtures thereof The bacteriocidal activity of the ophthalmic solutions of Example 1, above, were comparatively tested as follows. Solutions were made up generally according to Example 1. Specifically, a solution was made according to Example 1 with PVP Kollidon® K-25, with Kollidon® 30, and with Kollidon® 17 and 90 as the sole PVP sources. Another solution was made according to Example 1, but without any PVP.

The microorganism C. albicans (ATCC 10231) was selected for testing. With respect to the test solutions, they were first stored for approximately 14 days at 45° C. before such microorganisms were exposed to each solution.

TABLE I

Average log-drops at specified time intervals for Solutions of Example 1 with different PVP's and no PVP

| ORGANISM | Contact Time | Kolli-don ® 17 | Kolli-don ® 25* | Kolli-don ® 30* | Kolli-don ® 90* | Purite only |
|---|---|---|---|---|---|---|
| C. albicans | 0 hr. | $7 \times 10^5$ | $7 \times 10^5$ | $7 \times 10^5$ | $7 \times 10^5$ | $7 \times 10^5$ |
| | 1 hr. | $7 \times 10^5$ | $5 \times 10^5$ | $2 \times 10^5$ | $7 \times 10^5$ | $6 \times 10^5$ |
| | 2 hr. | $4 \times 10^5$ | $6 \times 10^2$ | $4 \times 10^2$ | $6 \times 10^5$ | $5 \times 10^5$ |
| | 6 hr. | $2 \times 10^5$ | $1 \times 10^2$ | <10 | $5 \times 10^5$ | $5 \times 10^5$ |

*Manufactured by BASF Aktiengesellschaft, Ludwigshafen, Germany

With reference to Table 1 above, there is shown about a 3 log kill decrease as against C. albicans at 2 hours when K-25 and K-30 were present in the solution. This log kill can be readily compared to the relatively insignificant log kill decrease at 2 and 6 hours for the solutions containing Purite™ only, Purite™ plus K-17, and Purite™ plus K-90. K-17 does not have aldehyde end groups which react with Purite™, and K-90 is a type of PVP having very few aldehyde end groups and a molecular weight well over 100,000 daltons.

Standard culture methods, harvest and quantitative microbiological analysis techniques were used. Log kill was determined after 1, 2 and 6 hour's contact with the microorganism using the standard method for log kill determination. See Pflug IJ, Holcomb RG, "Principles of Thermal Destruction of Microorganisms" in: Block SS, ed. Disinfection, Sterilization, and Preservation, 3rd ed., Philadelphia, Lea & Febiger, 1983:751–810; Houlsby RD, "An Alternative Approach for Preservative Testing of Ophthalmic Multiple-dose Products", J. Parenter Drug Assoc. 1980; 34(4):272–6; and Bruch MK, "The Regulation of Hydrophilic Contact Lenses by the Food and Drug Administration", Dev. Ind. Microbiol., 1976; 17:29–47.

In view of the results set forth in Table 1 above, it is believed that chlorite ions react with (oxidizes) the reactive end groups of the PVP molecules which are, preferably, aldehyde end groups thereby providing more kill. The results further indicate that K-25 and K-30 grades of PVP (those having a molecular weight of about 29,000 daltons and about 45,000 daltons, respectively, and having reactive end groups) are extremely effective against the test organism, C. albicans, yielding about 3.8 and 5.8 logs of reduction, respectively, at six hours. Thus, with respect to the solution of this invention, it is preferred that the amount and grade of the reactive end group PVP of this invention be sufficient to exhibit antimicrobial activity wherein there is at least about 3 log kill at six hours against C. albicans.

It has been found that the formulation should preferably not be used immediately after mixing, but rather after sufficient time has passed after mixing to allow the components to react. Preferably, the formulation should not be used until after 24 hours after mixing.

In addition, the present invention is directed to a method for disinfecting and cleaning a contact lens. The method comprises first forming an ophthalmically acceptable solution comprising an oxidizing agent and a reactive end group PVP having a molecular weight ranging from about 10,000 to about 100,000 daltons. After forming the solution, a contact lens is contacted with the solution. The lens is contacted with the solution for a period of time sufficient to disinfect the lens, i.e., time in which will reduce and/or eliminate the microbial burden on a contact lens when used in a contact lens care regimen which includes a recommended soaking time (FDA Chemical Disinfection Efficacy Test—July, 1985 Contact Lens Solution Draft Guidelines). More preferably, the lens should be soaked in the solution for a period of time ranging from about 1 to 8 hours. An exemplar solution useable in the method of this invention is the same as the solution described in Example 1 above.

After contacting the lens with the solution for the preferred amount of time, it is preferable to rinse the solution from the lens with a buffered saline solution or with the disinfecting solution itself, for example, before placing the lens in the eye.

It should also be appreciated that use of a reactive end group PVP together with the oxidizing agent provides a solution which is effective against A. fumigatus and bacteria.

As previously noted, certain end groups such as aldehydes preferably functionalize the PVP whereas other end groups such as t-butyl alcohol should not be present to any significant extent as functional groups on the PVP. In this regard, the bacteriocidal activity of the ophthalmic solution of Example 2 below was comparatively tested as follows. Solutions were made up generally according to Example 2. Specifically, a solution was made according to Example 2 with PVP having aldehyde end groups and PVP having t-butyl alcohol end groups. Another solution was made according to Example 2, but without any PVP.

The microorganism was selected and tested as noted above with respect to Example 1 and Table I, and average log-drops were tabulated as set forth in Table II below.

EXAMPLE 2

| Ingredients | % (w/v) |
| --- | --- |
| Sodium chloride | 0.62 (w/v) |
| Boric acid | 0.473 (w/v) |
| Sodium borate | 0.090 (w/v) |
| Sodium chlorite* | 0.0223% (w/v) |
| PVP, K-30** | 0.50 (w/v) |

*technical grade
**PVPs containing different end-groups as noted in the text.

TABLE II

Average log-drops at specified time intervals for Solutions of Example 2 with Purite only, t-Bu PVP and aldehyde PVP

| ORGANISM | Contact Time (hr) | Purite only | PVP with t-Bu end groups | PVP with Aldehyde end groups |
| --- | --- | --- | --- | --- |
| C.albicans | 0 hr. | $5 \times 10^5$ | $5 \times 10^5$ | $5 \times 10^5$ |
|  | 2 hr. | $5 \times 10^5$ | $5 \times 10^5$ | $4 \times 10^5$ |
|  | 4 hr. | $5 \times 10^5$ | $5 \times 10^5$ | <10 |
|  | 6 hr. | $5 \times 10^5$ | $5 \times 10^5$ | <10 |

It can be concluded that the PVP having t-butyl end groups does not display significant increased efficacy against C. albicans; whereas, the PVP with aldehyde end groups does.

Having thus described exemplary embodiments of the present invention, it should be noted by those skilled in the art that the within disclosures are exemplary only and that various other alternatives, adaptations and modifications may be made without departing from the spirit and scope of the present invention. Accordingly, the present invention is not limited to the specific illustrative embodiments illustrated herein, but is only limited by the following claims.

What is claimed is:

1. A method of disinfecting and cleaning a contact lens, comprising the step:

contacting a contact lens with a solution consisting essentially of:

an oxidizing agent wherein the oxidizing agent is a source of chlorite ions, and a polyvinyl pyrrolidone having a molecular weight ranging from 10,000 to 100,000 daltons, wherein said polyvinyl pyrrolidone comprises a plurality of reactive aldehyde end groups, and wherein said polyvinyl pyrrolidone does not contain t-butyl alcohol end groups.

2. The method according to claim 1, wherein at least about 50% of the end groups are reactive aldehyde end groups.

3. The method according to claim 1 wherein the polyvinyl pyrrolidone has a molecular weight of about 29,000.

4. The method according to claim 1 wherein the polyvinyl pyrrolidone has a molecular weight of about 45,000.

5. The method according to claim 1 wherein the pH of the solution is maintained from about 6.0 to about 8.5.

6. The method according to claim 1 wherein the oxidizing agent is sodium chlorite.

7. The method according to claim 6 wherein there is present in the solution from 0.008% (w/v) to 0.3% (w/v) sodium chlorite.

8. The method according to claim 7 wherein there is further present in the solution a total borate concentration of 0.2% (w/v) to about 2.0% (w/v).

* * * * *